United States Patent
Stährfeldt et al.

[11] Patent Number: 5,972,248
[45] Date of Patent: Oct. 26, 1999

[54] STABILIZERS BASED ON 1-AZA-2,2,6,6 TETRAMETHYBICYCLO [3.1.0]HEXANE

[75] Inventors: Thomas Stährfeldt, Neusäss; Josef Wiedemann, Zusmarshausen; Matthias Zäh, Gersthofen, all of Germany

[73] Assignee: Clariant GmbH, Frankfurt, Germany

[21] Appl. No.: 08/946,420

[22] Filed: Oct. 7, 1997

[30] Foreign Application Priority Data

Oct. 11, 1996 [DE] Germany ............... 196 41 905

[51] Int. Cl.⁶ ........... C09K 21/10; C07D 209/02
[52] U.S. Cl. ........... 252/601; 252/609; 252/384; 252/405; 252/501.1; 252/510; 524/94; 524/637.1; 544/198; 544/207; 544/209; 548/452; 548/512
[58] Field of Search .............. 548/452, 512; 544/198, 207, 209; 524/94, 637.1; 252/384, 405, 501.1, 510, 601, 609

[56] References Cited

U.S. PATENT DOCUMENTS

| | | | |
|---|---|---|---|
| 4,369,321 | 1/1983 | Cantatore | 546/187 |
| 4,419,472 | 12/1983 | Berner et al. | 524/102 |
| 4,501,837 | 2/1985 | Cantatore | 524/100 |
| 4,525,503 | 6/1985 | Cantatore | 524/98 |
| 5,633,378 | 5/1997 | Gaa et al. | 546/16 |

FOREIGN PATENT DOCUMENTS

| | | |
|---|---|---|
| 0031304 | 7/1981 | European Pat. Off. . |
| 0052579 | 5/1982 | European Pat. Off. . |
| 4423055 | 1/1996 | Germany . |

OTHER PUBLICATIONS

L.A. Krinitskaya, Izv. Akad. Nauk SSSR, Ser. Khim. 7 (1987) 1685; CAS 108:150284h.

Primary Examiner—Joseph K. McKane
Attorney, Agent, or Firm—Susan S. Jackson

[57] ABSTRACT

The present invention relates to novel stabilizers of the formula (I)

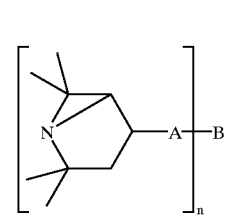

in which the substituents have the meaning defined in the description.

These novel stabilizers are particularly suitable for stabilizing organic material, such as plastics, oils, paints and coatings, against degradation by light, radiation, heat and oxygen.

13 Claims, No Drawings

STABILIZERS BASED ON 1-AZA-2,2,6,6 TETRAMETHYBICYCLO [3.1.0] HEXANE

DESCRIPTION

Novel stabilizers based on 1-aza-2,2,6,6-tetramethylbicyclo[3.1.0]hexane

It is known that organic materials are damaged by light, radiation, heat or oxygen. There are already many publications which describe compounds for stabilizing organic material. In connection with polyolefins, these are usually compounds based on sterically hindered phenols, organic phosphites, α-hydroxybenzophenone, hydroxyphenylbenzotriazoles, nickel complexes or 2,2,6,6-tetraalkylpiperidine (cf. R. Gächter, H. Müller, Plastics Additives Handbook, 3rd Edition, Hanser Verlag, Munich 1990).

The classes of compound mentioned often have specific disadvantages, which arise alongside the desired stabilizing action. There is a great demand for novel classes of stabilizer, in particular in respect of color properties, interaction with pigments, compatibility of the various stabilizers with one another and with the material to be stabilized, resistance to chemicals and water (sensitivity to hydrolysis), storage stability, migration properties and improvement in the stabilization against the damaging influences of heat and light during long-term use.

The object of the present invention was thus to provide novel stabilizers which do not have the disadvantages described.

It has been found, surprisingly, that suitable derivatives of 1-aza-2,2,6,6-tetramethylbicyclo[3.1.0]hexane (I) are capable of excellently stabilizing organic materials against the damaging influence of light, radiation, heat and oxygen.

The invention thus relates to novel stabilizers which can be described by the formula (I):

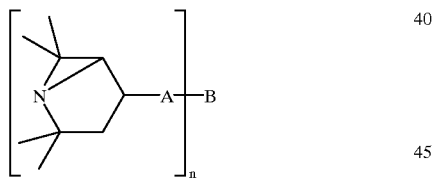

I in which
n is 1 or 2,
A is:
—O—C(O)—, —O—C(O)—N(H)—, —N(R¹)—C(O)—, —N(R¹)—C(O)—N(H)— or a direct bond, preferably —O—C(O)— or —O—C(O)—N(H)—,
B is, if A is a direct bond:
for n 1: —N(R¹R²) or —O—R¹,
for n=2: —N(R¹)—,
B is, if A is not a direct bond:
for n=1: $C_2$–$C_{18}$-alkyl, preferably $C_8$–$C_{16}$-alkyl, $C_3$–$C_{10}$-cycloalkyl, preferably $C_4$–$C_8$-cycloalkyl, or $C_6$–$C_{18}$-aryl or $C_7$–$C_{18}$-arylalkyl, preferably $C_6$–$C_{10}$-aryl or $C_7$–$C_{10}$-arylalkyl, which are substituted by —CN, —NO₂, amine or halogen, or a heteroaromatic radical having 5–15 carbon atoms, preferably 6–10 carbon atoms,
for n=2: $C_2$–$C_{18}$-alkylene, preferably $C_4$–$C_8$-alkylene, or $C_6$–$C_{18}$-arylene or $C_7$–$C_{18}$-arylalkylene, preferably $C_6$–$C_{10}$-arylene or $C_7$–$C_{10}$-arylalkylene, which are substituted by —CN—NO₂, amine or halogen, or a heteroaromatic radical having 5–15 carbon atoms, preferably 6–10 carbon atoms.

$R^1$ is:
H, a substituted $C_1$–$C_{18}$-alkyl or -alkylene, preferably a $C_2$–$C_8$-alkyl or -alkylene substituted by a derivative of triazine or by an amine, or a $C_1$–$C_{18}$-alkyl substituted by a derivative of 1-aza-2,2,6,6-tetramethylbicyclo[3.1.0]hexane, $C_3$–$C_{10}$-cycloalkyl, or $C_6$–$C_{18}$-aryl or $C_7$–$C_{18}$-arylalkyl, preferably $C_6$–$C_{10}$-aryl or $C_7$–$C_{10}$-arylalkyl, which are substituted by —CN, —NO₂, amine or halogen, or a heteroaromatic radical having 5–15 carbon atoms, preferably 6–10 carbon atoms.

$R^2$ is:
H, a substituted $C_1$–$C_{18}$-alkyl, preferably a $C_2$–$C_8$-alkyl, substituted by a derivative of triazine or by an amine, $C_3$–$C_{10}$-cycloalkyl, or $C_6$–$C_{18}$-aryl or $C_7$–$C_{18}$-arylalkyl, preferably $C_6$–$C_{10}$-aryl or $C_7$–$C_{10}$-arylalkyl, which are substituted by —CN, —NO₂, amine or halogen, or a heteroaromatic radical having 5–15 carbon atoms, preferably 6–10 carbon atoms, or a derivative of triazine, preferably a derivative of triazine of the formula $T_1$ or $T_2$.

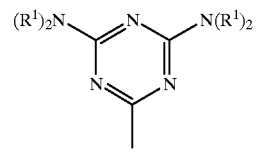

$T_1$

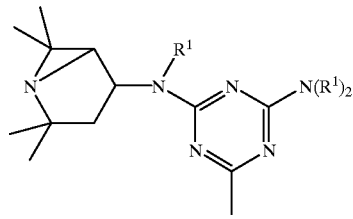

$T_2$

The heteroaromatic radicals mentioned contain up to 3, preferably 1 or 2, heteroatoms. The heteroatoms used are O, S and N, preferably N.

The present invention furthermore relates to the nature of the preparation of these novel compounds, and furthermore to the use of the novel compounds as stabilizers for organic material against the damaging influence of light, radiation, heat and oxygen.

Compound II has been prepared in a two-stage synthesis and in a good yield starting from 2,2,6,6-tetramethyl-4-oxo-piperidine, analogously to the instructions from the literature (L. A. Krinitskaya, Izv. Akad. Nauk SSSR, Ser. Khim. 7 (1987) 1685; CAS 108:150284h).

FIG. 1: General synthesis equation of the compounds according to the invention starting from 1-aza4-oxo-2,2,6,6-tetramethylbicyclo[3.1.0]hexane (II).

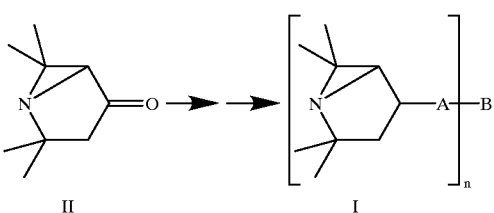

It has been found that the keto function in II is accessible for further reactions. For example, it can be reduced to the corresponding alcohol (III) or, secondly, reacted with amines to give corresponding imines (IV). The imine can be reduced further to give the corresponding amine (V) (FIG. 2).

FIG. 2: General synthesis equation of the process according to the invention for the preparation of the precursors III and V. $R^1$ has the abovementioned meaning.

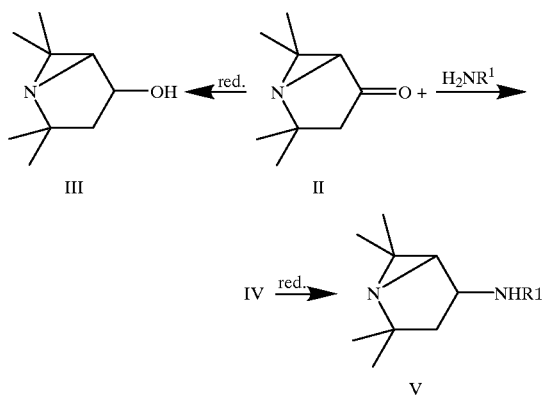

When considering products III and V, it is apparent that they are each diasteromer pairs. The diastereomers of the compound III were separated from one another. The secondary reactions of III were carried out with a pure diastereomer and with the mixture of the two diastereomers, and the secondary reactions of V were carried out only with the mixture of the two diastereomers.

In contrast to precursor II described above, the invention relates to the compounds III, IV and V. These compounds are alcohols (III) or primary or secondary amines (V) (depending on whether $R^1$ is an H atom or one of the other radicals listed in more detail above). These compounds III and V according to the invention can be reacted with a suitable reagent to give the compound I, which is likewise according to the invention.

The reaction of 2,2,6,6-tetramethyl-4-oxo-piperidine II with an amine to give the corresponding imine of the type IV can be carried out, for example, in an aprotic, organic solvent, preferably a hydrocarbon, or in an ether, in particular in methyl tert-butyl ether. The amine can be employed stoichiometrically or in excess. Another possibility comprises using the amine in excess as the solvent. The reaction can also be catalyzed by an acidic compound, such as, for example, by organic acids, in particular by p-toluenesulfonic acid. A temperature which is higher than 20° C. is chosen as the reaction temperature, and the temperature of the boiling point of the solvent used is particularly suitable.

The reduction of an imine of the type IV to give the corresponding amine of type V and the reduction of the 2,2,6,6-tetramethyl-4-oxo-piperidine II to give the corresponding alcohol 2,2,6,6-tetramethyl-4-hydroxy-piperidine III can be carried out in a protic or aprotic, organic solvent, preferably in tetrahydrofuran or an alcohol, in particular in methanol or ethanol, or in mixtures of these suitable solvents. A complex hydride, in particular $NaBH_4$, can be used as the reducing agent, and this is preferably employed stoichiometrically or in a slight excess, based on the imine or the ketone. For working up, the solvent can be removed by distillation, a polar solvent can be added to the residue and the product can be extracted with an organic solvent. A suitable polar solvent is preferably water, but in particular an aqueous solution of an inorganic salt, preferably NaCl. A suitable organic solvent for the extraction is preferably an organic solvent which is not miscible with water, in particular an ether, such as, for example, methyl tert-butyl ether.

The reaction of the alcohol 2,2,6,6-tetramethyl-4-hydroxy-piperidine III or the amine of type V to give the compounds I according to the invention is carried out in an aprotic, organic solvent, preferably a hydrocarbon, in particular aromatic hydrocarbons, such as, for example, toluene or xylene, or in mixtures thereof, or in tetrahydrofuran. Another possibility is to use one of the reaction components in excess as the solvent. These suitable reaction components are compounds which are known to react with alcohols or primary or secondary amines under suitable conditions. Such compounds are, for example, mono- or difunctional isocyanates, which are optionally further substituted, esters, acid halides, acid anhydrides, alkyl halides and halogen-substituted triazines.

The compounds according to the invention are outstandingly suitable for stabilizing organic material against the action of light, radiation, oxygen and heat. They are added to the organic material to be stabilized in a concentration of 0.001 to 5% by weight, preferably 0.02 to 1.0% by weight, based on the organic material, before or after its preparation.

Organic material is to be understood as meaning, for example, precursors for plastics, coatings, paints and oils, but in particular plastics, coatings, paints and oils themselves.

The present invention furthermore relates to organic materials, in particular plastics, coatings, paints and oils, which are stabilized against the action of light, radiation, oxygen and heat and comprise the compound(s) claimed in this Application in the abovementioned concentrations. These organic materials include, for example, substances such as are described in DE P 4423055.9, pages 13–18.

If appropriate, the organic material stabilized by the compounds according to the invention can also comprise further additives, for example antioxidants, light stabilizers, metal deactivators, antistatic agents, flame retardants, pigments and fillers. Antioxidants and light stabilizers which are added in addition to the compounds according to the invention are, for example, compounds based on sterically hindered amines; antioxidants are, for example, sterically hindered phenols, or costabilizers containing sulfur or phosphorus.

Possible suitable additional additives are, for example, compounds such as are described in DE P 4423055.9, pages 18–29. Possible further suitable additives are additionally 2,2',2"-nitrilo[triethyl-tris(3,3',5,5'-tetra-tert-butyl-1,1'-biphenyl-2,2'-diyl)phosphite], bis[2-methyl-4,6-bis(1,1-dimethylethyl)phenol]phosphorous acid ethyl ester, secondary hydroxylamines, such as, for example, distearylhydroxylamine or dilaurystearylamine, zeolites, such as, for example, DHT 4A, oxides and hydroxides of aluminum, zinc, alkali metals and alkaline earth metals, fine-grained material being specifically suitable in particular for individual applications, Al stearate, Ca stearate, Mg stearate or Zn stearate, fine-grained material being specifically suitable in particular for individual applications, the condensation product of N,N'-bis[(4,6-di(4-n-butylamino-2,2,6,6-tetramethylpiperid-4-yl)1,3,5-triazin-2-yl]-3-aminopropyl-ethylene-1,2-diamine and 2,4-dichlor-6-(4-n-butylamino-2,2,6,6-tetramethyl-piperid-4-yl)1,3,5-triazine, 1,3,-2,4di(benzylidene)-D-sorbitol, 1,3-2,4-di-(4-tolylidene)-D-sorbitol, 1,3-2,4-di(4-ethylbenzylidene)-D-sorbitol.

Hydrotalcites, which can be described by the formula $$[(M^{2+})_{1-x}(M^{3+})_x(OH)_2(A^{n-})_{x/n}yH_2O],$$

in which
$(M^{2+})$ is Mg, Ca, Sr, Ba, Zn, Pb, Sn, or Ni,
$(M^{3+})$ is Al, B, or Bi,
$A^n$ is an anion of valency n,
n is an integer from 1 to 4,
x is a value between 0 and 0.5,
y is a value between 0 and 2,
A is $OH^-$, $Cl^-$, $Br^-$, $I^-$, $ClO^{4-}$, $CH_3COO^-$, $C_6H_5COO^-$, $CO_3^{2-}$, $SO_4^{2-}$, $(OOC-COO)^{2-}$, $(CHOHCOO)_2^{2-}$, $(CHOH)_4CH_2OHCOO^-$, $C_2H_4(COO)_2^{2-}$, $(CH_2COO)_2^{2-}$, $CH_3CHOHCOO^-$, $SiO_3^{2-}$, $SiO_4^{4-}$, $Fe(CN)_6^{3-}$, $Fe(CN)_6^{4-}$, $BO_3^{3-}$, $PO_3^{3-}$, or $HPO_4^{2-}$,
can also be a constituent of the mixture.

Hydrotalcites in which $(M^{2+})$ is $(Ca^{2+})$, $(Mg^{2+})$ or a mixture of $(Mg^{2+})$ and $(Zn^{2+})$; and $(A^{n-})$ is $CO_3^{2-}$, $BO_3^{3-}$, or $PO_3^{3-}$ are preferably employed.

x has a value of 0 to 0.5 and y has a value of 0 to 2.

Hydrotalcites which can be described by the formula $$[(M^{2+})_x(Al^{3+})_2 (OH)_{2x+6nz}(A^{n-})_2yH_2O]$$

can furthermore also be employed.

In this formula, $(M^{2+})$ is $Mg^{2+}$ or $Zn^{2+}$, but preferably $Mg^{2+}$.

$(A^{n-})$ is an anion, in particular from the group consisting of $CO_3^{2-}$, $(OOC-COO)^{2-}$, $OH^-$ and $S^{2-}$, in which n describes the valency of the ion.

y is a positive number between 0 and 5, in particular between 0.5 and 5;

x and z have positive values, which should be between 2 and 6 in the case of x and less than 2 in the case of z. The hydrotalcites of the following formulae are to be regarded as particularly preferred:

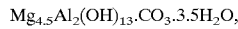

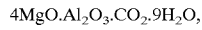

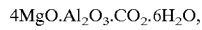

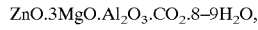

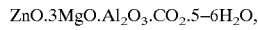

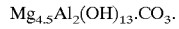

Hydrotalcites are preferably employed in the polymer in a concentration of 0.01 to 5% by weight, in particular 0.2 to 3% by weight, based on the total polymer formulation.

The additives are incorporated into the organic polymers by generally customary methods. The incorporation can be carried out, for example, by mixing or applying the compounds and, if appropriate, further additives into or onto the polymer immediately after the polymerization or into the melt before or during shaping. The incorporation can also be carried out by application of the dissolved or dispersed compounds to the polymer directly or by mixing them into a solution, suspension or emulsion of the polymer, if appropriate with subsequent evaporation of the solvent. The compounds are also active if they are incorporated subsequently into an already granulated polymer in a separate processing step. The compound(s) of the formula (I) according to the invention can also be added in the form of a masterbatch, which comprises this/these compound(s), for example, in a concentration of 1 to 75, preferably 2.5 to 30% by weight, to the polymer to be stabilized.

EXAMPLES

The following examples are intended to illustrate the invention in more detail. All compounds could be identified unambiguously with the aid of their $^1$H- or $^{13}$C-NMR spectra. The syntheses were carried out with commercially obtainable starting materials.

1. Preparation of the educts which are not according to the invention 1.1. Preparation of N-chloro-2,2,6,6-tetramethyl-4-oxo-piperidine (M=189.7 g/mol)

500.0 g (2.10 mol) of dichloroisocyanuric acid Na salt dihydrate are dissolved in 1800 ml of water and the solution is slowly added to a solution of 296.0 g (1.909 mol) of 2,2,6,6-tetramethyl-4-oxo-piperidine in 1000 ml of water at 45° C., while stirring (10 minutes). The thinly liquid, slightly yellow suspension is subsequently stirred at 30° C. for 180 minutes. After addition of 760 ml of toluene, it is stirred intensively at 25° C. for a further 90 minutes. The solid is filtered off and washed with 300 ml of toluene. After the organic phase has been separated off, the aqueous phase is extracted by shaking three times with 200 ml of toluene each time. The organic phases are combined, dried with sodium sulfate, filtered off from this and freed from the solvent in vacuo. The crude yield (359.0 g; 1.89 mol; 99%; orange oil) is distilled under a reduced pressure. 333.0 g (1.76 mol, 92%) of product are isolated at a discharge temperature of 112° C./0.01 mbar (pale yellow oil).

1.2. Preparation of 1-aza-4-oxo-2,2,6,6-tetramethylbicyclo [3.1.0]hexane (II) (M=153.2 g/mol)

450 g of a 30% strength methanolic sodium methanolate solution (135.0 g of NaOMe, 2.50 mol) are added to a solution of 379.4 g (2.0 mol) of N-chloro-2,2,6,6-tetramethyl-4-oxo-piperidine in 980 ml of methanol at 66° C. in the course of 80 minutes, while stirring. After the end of the dropwise addition, the solution is stirred at 66° C. for 150 minutes. The solid is filtered at 20° C. and washed with 100 ml of methanol. The filtrate is freed from the solvent at 50° C. under 20 mbar. 300 ml of 10% strength NaCl solution are added to the residue and the mixture is extracted by shaking three times with 200 ml of methyl tert-butyl ether each time. The combined organic phases are dried with sodium sulfate, filtered off from this and freed from the solvent under 12 mbar. The orange oil which remains is distilled under a reduced pressure. 276.0 g (1.80 mol, 90%) of product are isolated at a discharge temperature of 82° C./15 mbar (golden yellow oil).

2. Preparation of products III, D and E according to the invention

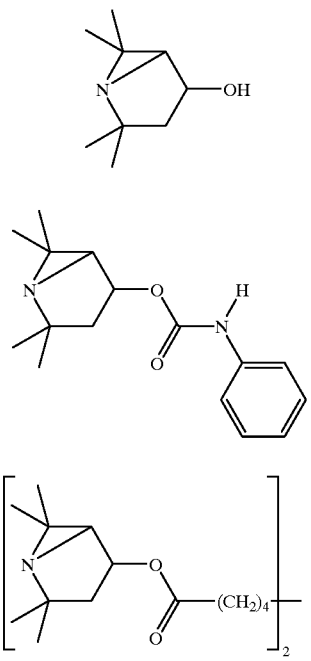

2.1. Preparation of 1-aza-4-hydroxy-2,2,6,6-tetramethylbicyclo[3.1.0]hexane (III) (M 155.27 g/mol)

60.4 g (1.60 mol) of $NaBH_4$ are added in portions to a solution of 306.4 g (2.00 mol) of 1-aza-4-oxo-2,2,6,6-tetramethylbicyclo[3.1.0]hexane (II) in 1000 ml of ethanol at 20° C., while cooling (20 minutes). The mixture is stirred at 20° C. for 120 minutes and at 50° C. for a further 120 minutes, and after the evolution of gas, a milky white mixture forms. The solvent is removed under 12 mbar at 60° C. 300 ml of 10% strength NaCl solution are added to the residue and the mixture is extracted by shaking three times with 200 ml of methyl tert-butyl ether each time. The combined organic phases are dried with sodium sulfate, filtered off from this and concentrated under 12 mbar/75° C. One of the diastereomers crystallized out, in the form of colorless crystals, from the crude yield of 270.3 g (1.74 mol; 87%) after 18 hours at 20° C. The isomer mixture is stirred with 50 g of 3-pentanone and the insoluble fraction is filtered off (132.6 g; 0.854 mol; 43%; melting point=114–116° C.; diastereomer ratio according to GC: 91:9). The solid product is recrystallized from 3-pentanone. Yield: 114.6 g (0.734 mol); melting point=120–121° C.; $^{13}C\{^{1}H\}$-NMR ($CDCl_3$): δ=18.6, 25.3, 29.5, 33.7, 40.8, 46.6, 53.4, 62.6, 71.9 ppm.

The filtrate is freed, from the solvent under 12 mbar/50° C. The second product fraction is isolated as a pale yellow, cloudy oil (112.2 g; 0.721 mol; 36%; diastereomer ratio according to GC: 46:54). According to $^{1}H$- and $^{13}C$-NMR, the content obtained as an oil is a mixture of the two diastereomers.

2.2. Preparation of compound D (M=274.40 g/mol)

26.2 g (0.22 mol) of phenyl isocyanate are slowly added to a solution of 31.1 g (0.2 mol) of 1-aza-4-hydroxy-2,2,6,6-tetramethylbicyclo[3.1.0]hexane (III) in 100 ml of toluene at 25° C., while stirring; during this operation, the mixture heats up to 50° C. After the mixture has been stirred at 45° C. for 30 minutes, severe clouding results, and in the course of stirring at 25° C. for a further 200 minutes, a thick precipitate separates out. The precipitate is filtered off with suction over a glass sintered frit, washed with 50 ml of toluene and 100 ml of hexane and dried at 100° C. in vacuo. Yield: 45.1 g(0.164 mol; 82%), colorless crystals, melting point: 146° C.

2.2. Preparation of compound E (M=448.72 g/mol)

A mixture of 23.0 g (0.10 mol) of dimethyl sebacate, 35.7 g (0.23 mol) of 1-aza-4-hydroxy-2,2,6,6-tetramethylbicyclo [3.1.0]hexane (III) (the crystalline portion with a diastereomer ratio of 91:9 is used) and 0.15 g of lithium amide in 250 ml of heptane is stirred at 98° C. for 6 hours, the methanol slowly formed being removed continuously from the equilibrium. The mixture is extracted by shaking with water at 95° C. The organic phase is separated off from the aqueous phase at 95° C., dried with sodium sulfate, filtered off from this and freed from the solvent under 12 mbar/50° C. Yield: 44.1 g (0.098 mol; 98%), colorless oil, boiling point 287° C., pure in the $^{13}C$-NMR (carbonyl signal in $CDCl_3$ at δ=172.74 ppm).

The experiment was carried out analogously with the oily product III (diastereomer ratio of 46:54). Yield: 86%, colorless oil.

3. Preparation of the compounds of type IV according to the invention

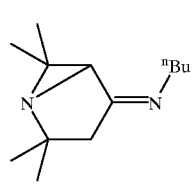

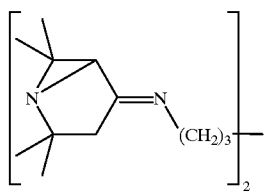

3.1. Preparation of compound F (M=208.39 g/mol)

A solution of 80.0 g (0.523 mol) of 1-aza-4-oxo-2,2,6,6-tetramethylbicyclo[3.1.0]-hexane (II), 38.3 g (0.523 mol) of n-butylamine, 85.2 g (0.575 mol) of triethyl orthoformate, and 0.3 g of p-toluenesulfonic acid in 260 ml of methyl tert-butyl ether is stirred at 62° C. for 13 hours. The golden yellow, clear solution is freed from the solvent under a pressure of 50 mbar at 40° C. The liquid crude product is distilled in vacuo; the product is isolated as a golden yellow, clear oil at a discharge temperature of 118° C./15 mbar (89.0 g; 0.429 mol; 82%).

3.2. Preparation of compound G (M=386.70 g/mol)

A mixture of 76.6 g (0.5 mol) of 1-aza4-oxo-2,2,6,6-tetramethylbicyclo-[3.1.0]hexane (II), 29.1 g (0.25 mol) of hexamethylenediamine, 92.0 g (0.612 mol) of triethyl orthoformate and 0.4 g of p-toluenesulfonic acid in 250 ml of methyl tert-butyl ether is stirred at 66° C. for 10 hours. The golden yellow, clear solution is concentrated at 50° C. under 25 mbar and the oil which remains is distilled under reduced pressure. The product is isolated at a discharge temperature of 174° C. (0.008 mbar). Yield: 69.3 g (0.179 mol; 72%), orange, clear oil.

4. Preparation of the compounds of type V

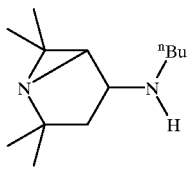
H

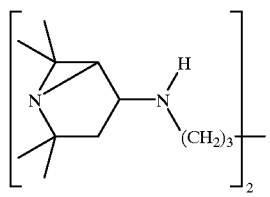
J

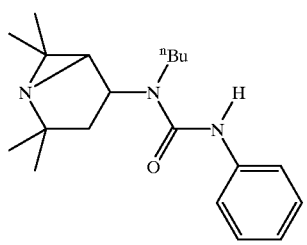
K

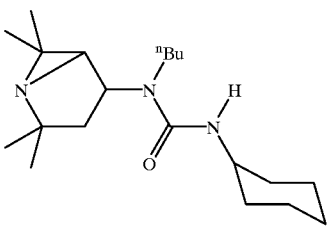
L

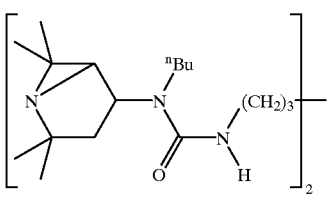
M 4.1. Preparation of 1-aza-4-(n-butylamino)-2,2,6,6-tetramethylbicyclo[3.1.0]-hexane (H) (M=210.41 g/mol)

15.8 g (0.418 mol) of $NaBH_4$ are added in small portions to a solution of 87.0 g (0.417 mol) 1-aza4-(n-butylimino)-2,2,6,6-tetramethylbicyclo-[3.1.0]hexane (F) in 290 ml of methanol at 16° C., while cooling. After 120 minutes, the batch heats up to 38° C. without external heating (gentle evolution of gas). It is then cooled, and stirred at 25° C. for a further 240 minutes. The solvent is removed under 50 mbar/50° C. 200 ml of toluene are added to the residue and the mixture is extracted by shaking twice with 100 ml of 20% strength NaCl solution each time. The organic phase is dried with sodium sulfate and filtered off from this. The product is distilled in vacuo. The product is isolated as a colorless, thinly liquid oil at a discharge temperature of 93° C./0.04 mbar (69.6 g; 0.331 mol; 79%).

4.2. Preparation of compound J (M 390.74 g/mol)

7.4 g (0.196 mol) of $NaBH_4$ are added in portions to a solution of 69.0 g (0.178 mol) of compound G in 240 ml of methanol at 12° C., while cooling.

The mixture is stirred at 67° C. for 10 hours. After removal of the solvent under 25 mbar at 50° C., 200 ml of methyl tert-butyl ether are added to the residue and the mixture is extracted by shaking three times with 100 ml of a 10% strength NaCl solution each time. The organic phase is dried with sodium sulfate, filtered off from this and freed from the solvent under 25 mbar/50° C. The crude yield (61.0 g; 88%; brown oil) is distilled in vacuo. The product is isolated as a golden yellow, highly viscous oil at a discharge temperature of 174° C./0.015 mbar (45.0 g; 65%).

4.3. Preparation of compound K (M=328.53 g/mol)

13.1 g (0.11 mol) of phenyl isocyanate are added dropwise to a solution of 21.0 g (0.1 mol) of 1-aza4-(n-butylamino)-2,2,6,6-tetramethylbicyclo[3.1.0]-hexane (H) in 75 ml of toluene at 24° C. in the course of 5 minutes, while stirring vigorously. During this operation, the solution heats up to 68° C. without external heating. The thoroughly stirred mixture cools to 32° C. in the course of 30 minutes, and the solvent is then removed under 25 mbar/50®C. The crude product (35.5 g; >100%; brown oil) is distilled in vacuo. The product is isolated as a golden yellow, highly viscous oil at a discharge temperature of 172° C./0.05 mbar (31.5 g; 0.096 mol; 96%).

4.4. Preparation of the compound L (M=333.58 g/mol)

13.8 g (0.11 mol) of cyclohexyl isocyanate are added dropwise to a solution of 21.0 g (0.10 mol) of 1-aza4-(n-butylamino)-2,2,6,6-tetramethylbicyclo[3. 1.0]-hexane (H) in 75 ml of toluene at 22° C. in the course of 5 minutes, while stirring vigorously. During this operation, the solution heats up to 50° C. without external heating. The thoroughly stirred mixture cools to 22° C. in the course of 25 hours, and the solvent is then removed under 25 mbar/50° C. The crude product (35.8 g; >100%; brown oil) is distilled in vacuo. The product is isolated as a pale yellow, highly viscous oil at a discharge temperature of 158° C./0.005 mbar (30.0 g; 0.090 mol; 90%).

4.5. Preparation of compound M (M=589.04 g/mol)

8.4 g (0.05 mol) of hexamethylene diisocyanate are added dropwise to a solution of 21.0 g (0.1 mol) of 1-aza4-(n-butylamino)-2,2,6,6-tetramethylbicyclo[3.1.0]hexane (H) in 75 ml of toluene at 16° C. in the course of 5 minutes, while stirring vigorously. During this operation, the solution heats up to 36° C. without external heating. The thoroughly stirred, colorless mixture cools to 32° C. in the course of 30 minutes, and the solvent is then removed under 25 mbar/125° C. The product is isolated as a colorless, highly viscous oil (28.6 g; 0.049 mol; 98%). The $^1$H-NMR and $^{13}$C-NMR spectra agree with the expected structure and are clean (carbonyl signal in $CDCl_3$ at δ=152.93 ppm).

5. Light-stabilizing action in polypropylene films 100 parts by weight of non-stabilized polypropylene (®Hostalen PPK) were kneaded in a paddle kneader (manufacturer Brabender) at 200° C. and 20 rpm for 10 minutes together with 0.1 part by weight of calcium stearate, 0.05 part by weight of bis-3,3-bis-(4'-hydroxy-3'-tert-butylphenyl)-butanoic acid glycol ester (®Hostanox O 3), 0.1 part by weight of tris(2,4-di-tert-butylphenyl) phosphite (®Hostanox PAR 24) and 0.2 part by weight of the stabilizer to be tested. A film 100 μm thick was pressed from this mixture at 190° C. and the test specimen obtained in this manner was exposed to light in an accelerated weathering apparatus (®Xenotest 450). The change in the carbonyl index within this period of time was used as a criterion of the stability of the film. The carbonyl index CO was determined here in accordance with the equation $CO=E_{1720}/E_{2020}$ in which E is the extinction at the particular wavelength. For comparison purposes, a film was tested under the same conditions, but without the addition of a stabilizer according to the invention. The results of the experiments are summarized in Table 1:

Table 1: Change in the carbonyl index of films stabilized according to the invention

| Stabilizer | Time after which the carbonyl index increases by 1 unit (in hours) |
| --- | --- |
| No stabilizer | 350 hours |
| Stabilizer E1* | 1060 hours |
| Stabilizer E2** | 1990 hours |
| Stabilizer J | 830 hours |

*Product E prepared with the crystalline portion of product III
**Product E prepared with the oily portion of product III Table 1 underlines the very good light-stabilizing action of the stabilizers according to the invention in polypropylene.

We claim:

1. A novel stabilizer of the formula (I)

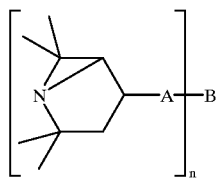

I in which
n is 1 or 2,
A is —O—C(O)—, —O—C(O)—N(H)—, —N($R^1$)—C(O)—, —N($R^1$)—C(O)—N(H)— or a direct bond,
B is, if A is a direct bond,
for n=1 —N($R^1R^2$) or —O—$R^1$,
for n=2 —N($R^1$)—,
B is, if A is not a direct bond,
for n=1 $C_2$–$C_{18}$-alkyl, $C_3$–$C_{10}$-cycloalkyl, or $C_6$–$C_{18}$-aryl or $C_7$–$C_{18}$-arylalkyl which are substituted by —CN, —$NO_2$, amine or halogen, or a heteroaromatic radical having 5–15 carbon atoms,
for n=2 $C_2$–$C_{18}$-alkylene, or $C_6$–$C_{18}$-arylene or $C_7$–$C_{18}$-arylalkylene which are substituted by —CN, —$NO_2$, amine or halogen, or a heteroaromatic radical having 5–15 carbon atoms,
$R^1$ is H, a $C_1$–$C_{18}$-alkyl or -alkylene substituted by a triazine compound, by a 1-aza-2,2,6,6-tetramethylbicyclo[3.1.0]hexane compound or by an amine, $C_3$–$C_{10}$-cycloalkyl, or $C_6$–$C_{18}$-aryl or $C_7$–$C_{18}$-arylalkyl which are substituted by —CN, —$NO_2$, amine or halogen, or a heteroaromatic radical having 5–15 carbon atoms, and
$R_2$ is H, a $C_1$–$C_{18}$-alkyl substituted by a triazine compound or by an amine, $C_3$–$C_{10}$-cycloalkyl, or $C_6$–$C_{18}$-aryl or $C_7$–$C_{18}$-arylalkyl which are substituted by —CN, —$NO_2$, amine or halogen, or a heteroaromatic radical having 5–15 carbon atoms, or a triazine compound.

2. A stabilizer as claimed in claim 1, in which
A is —O—C(O)— or —O—C(O)—N(H)—,
B is, if A is not a direct bond,
for n=1 $C_8$–$C_{16}$-alkyl, $C_4$–$C_8$-cycloalkyl, or $C_6$–$C_{10}$-aryl or $C_7$–$C_{10}$-arylalkyl, which are substituted by —CN, —$NO_2$, amine or halogen, or a heteroaromatic radical having 6–10 carbon atoms,
for n=2 $C_4$–$C_8$-alkylene, or $C_6$–$C_{10}$-arylene or $C_7$–$C_{10}$-arylalkylene which are substituted by —CN, —$NO_2$, amine or halogen, or a heteroaromatic radical having 6–10 C atoms,
$R^1$ is H, a $C_2$–$C_8$-alkyl or -alkylene substituted by a triazine compound or by an amine, or $C_6$–$C_{10}$-aryl or $C_7$–$C_{10}$-arylalkyl which are substituted by —CN, —$NO_2$, amine or halogen, or a heteroaromatic radical having 6–10 carbon atoms, and
$R^2$ is H, a $C_2$–$C_8$-alkyl substituted by a triazine compound or by an amine, $C_3$–$C_{10}$-cycloalkyl, or a $C_6$–$C_{10}$-aryl or $C_7$–$C_{10}$-arylalkyl which are substituted by —CN, —$NO_2$, amine or halogen, or a heteroaromatic radical having 6–10 carbon atoms, or a triazine compound of the formula $T_1$ or $T_2$

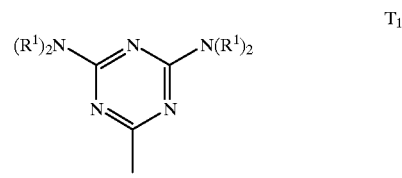

$T_1$

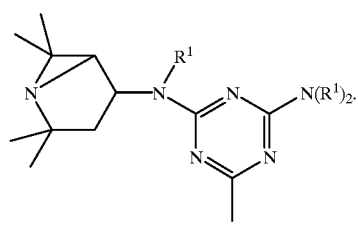

$T_2$

3. A process for the preparation of a compound of the formula (1) as claimed in claim 1, which comprises converting, in a first step, 1-aza4-oxo-2,2,6,6-tetramethylbicyclo[3.1.0]hexane (II) into an alcohol or amine of the formula (III) or (V),

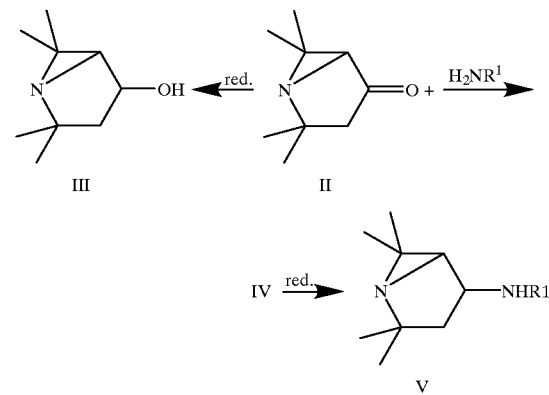

and reacting, in a second step, this reaction product with a mono- or difunctional isocyanate, which is optionally further substituted, ester, acid halide, acid anhydride, alkyl halide, halogen-substituted triazine or other compound which reacts with an alcohol or primary or secondary amine.

4. The process as claimed in claim 3, wherein the reaction is carried out in a protic or aprotic, organic solvent.

5. The process as claimed in claim 4, wherein the organic solvent is toluene, xylene or a mixture thereof or tetrahydrofuran.

6. The process as claimed in claim 3, wherein one of the reaction components is used in excess as the solvent.

7. A process of using the compound of the formula (I) as claimed in claim 1 for stabilizing organic material which is a precursor for plastics, coatings, paints and oils comprising adding a compound of the formula (I) as claimed in claim 1 to said organic material which is a precursor for plastics, coatings, paints and oils.

8. A process of using the compound of the formula (I) as claimed in claim 1 to stabilize polymeric material against degradation by light, radiation, heat and oxygen, comprising adding a compound of the formula (I) as claimed in claim 1 in a concentration of 0.001–5% by weight to the material to be stabilized.

9. The process as claimed in claim 8, further comprising adding at least one additive selected from the group consisting of antioxidants, light stabilizers, metal deactivators, antistatics, flame retardants, pigments and fillers.

10. The process as claimed in claim 8, wherein said compound is added in a concentration of 0.1–2.0% by weight.

11. The process as claimed in claim 7, wherein said organic material is selected from the group consisting of plastic, coating, paint and oil.

12. The process as claimed in claim 4, wherein said solvent is a hydrocarbon.

13. The process as claimed in claim 12, wherein said hydocarbon is an aromatic hydrocarbon.

* * * * *